(12) United States Patent
Wong et al.

(10) Patent No.: US 9,283,231 B2
(45) Date of Patent: Mar. 15, 2016

(54) SUSTAINED RELEASE FORMULATIONS FOR THE TREATMENT OF INTRAOCULAR PRESSURE OF GLAUCOMA

(71) Applicant: Icon Bioscience, Inc., Sunnyvale, CA (US)

(72) Inventors: Vernon G. Wong, Menlo Park, CA (US); Mae W. Hu, Los Altos Hills, CA (US); Glenn T. Huang, Fremont, CA (US)

(73) Assignee: Icon Bioscience, Inc., Sunnyvale, CA (US)

( * ) Notice: Subject to any disclaimer, the term of this patent is extended or adjusted under 35 U.S.C. 154(b) by 0 days.

(21) Appl. No.: 14/168,139

(22) Filed: Jan. 30, 2014

(65) Prior Publication Data

US 2014/0213646 A1 Jul. 31, 2014

Related U.S. Application Data

(60) Provisional application No. 61/759,129, filed on Jan. 31, 2013.

(51) Int. Cl.
*A61K 31/216* (2006.01)
*A61K 31/5575* (2006.01)
*A61K 9/00* (2006.01)
*A61K 47/14* (2006.01)

(52) U.S. Cl.
CPC ............ *A61K 31/5575* (2013.01); *A61K 9/0019* (2013.01); *A61K 9/0048* (2013.01); *A61K 47/14* (2013.01)

(58) Field of Classification Search
CPC .................................................. A61K 31/5575
USPC .......................................................... 514/530
See application file for complete search history.

(56) References Cited

U.S. PATENT DOCUMENTS

| 7,906,136 B2 | 3/2011 | Wong et al. |
| 2002/0193441 A1* | 12/2002 | Robertson ..................... 514/573 |
| 2006/0073182 A1 | 4/2006 | Wong et al. |
| 2011/0111006 A1 | 5/2011 | Wong et al. |
| 2012/0135984 A1 | 5/2012 | Delong et al. |
| 2012/0238857 A1 | 9/2012 | Wong et al. |

FOREIGN PATENT DOCUMENTS

WO  2013058838 A2  4/2013

OTHER PUBLICATIONS

International Search Report and Written Opinion, mailed May 13, 2014, and cited in related International application No. PCT/US2014/013744, filed Jan. 30, 2014.
International Preliminary Report on Patentability mailed, on Aug. 13, 2015, in related International Patent Application No. PCT/US2014/013744, filed Jan. 30, 2014.

* cited by examiner

*Primary Examiner* — Zohreh Fay
(74) *Attorney, Agent, or Firm* — Wiley Rein LLP

(57) ABSTRACT

The present embodiments provide for methods of treating elevated intraocular pressure or glaucoma using a sustained release medicament consisting of prostaglandin in benzyl benzoate that is injected intraocularly no more frequently than once every two months.

12 Claims, 3 Drawing Sheets

SUSTAINED RELEASE FORMULATIONS FOR THE TREATMENT OF INTRAOCULAR PRESSURE OF GLAUCOMA

RELATED APPLICATION

This application claims priority benefit of U.S. Application No. 61/759,129, filed Jan. 31, 2013, which is incorporated fully herein by reference.

BACKGROUND

Glaucoma is a leading cause of blindness in the world, and is commonly characterized by progressive optic neuropathy with associated visual field deficits. Estimates put the total number of suspected cases of glaucoma at over 70 million worldwide. Everyone is at risk for glaucoma, regardless of age: even though older people are at a higher risk for glaucoma, infants and children can suffer from glaucoma. High-risk groups include people over 60, family members of those already diagnosed, and people who are severely nearsighted.

Glaucoma usually results from fluid pressure building inside the eye until the optic nerve becomes damaged, leading to progressive, irreversible vision loss. The two main types of glaucoma are primary open-angle glaucoma and angle-closure glaucoma. Primary open-angle glaucoma causes 90% of glaucoma cases; its symptoms may include a loss of peripheral vision or tunnel vision. Symptoms of acute angle-closure glaucoma may include eye pain, blurred vision, nausea and/or vomiting, eye redness and seeing halos around lights. There are also low-tension or normal-tension forms, and congenital, pigmentary, and pseudoexfoliation forms of glaucoma. Secondary glaucoma can also develop as a complication from other medical conditions.

Although once sight is lost it cannot be recovered, it is possible, with treatment, to halt further vision loss caused by glaucoma. Glaucoma treatments include medicines, laser trabeculoplasty, conventional surgery, or a combination of any of these. Glaucoma medicines need to be taken regularly, and some medicines can cause headaches or other side effects. For example, drops may cause stinging, burning, and redness in the eyes. Because glaucoma often has no symptoms, people are often tempted to stop taking, or may forget to take, medicine. Compliance with eye drops regimens is especially problematic for the elderly. There remains a need for sustained release formulations for delivering glaucoma treatments.

SUMMARY

The embodiments described herein provide for sustained release pharmaceutical formulations for treatment of high intraocular pressure and glaucoma. More specifically, formulations consisting of a prostaglandin in a benzyl benzoate can be injected into the vitreous of the eye, where sustained release of prostaglandin lasts for at least two months, lowering intraocular pressure and maintaining that lower pressure. In an alternative embodiment, the formulation can be injected directly into the anterior chamber of the eye. Indeed, kinetic studies have demonstrated that particular formulations of latanoprost in benzyl benzoate can provide for sustained release of latanoprost for over six months with a single intraocular injection.

The length of time over which the release of the prostaglandin is sustained correlates with the concentration of prostaglandin in the formulation: higher concentrations of prostaglandin provide for longer sustained release. The length of time over which the release of the prostaglandin is sustained also correlates with the size of the dose administered: a larger dosage unit (volume) provides for a longer sustained release of active agent. The unit dose volume for intravitreal injection (or injection into the anterior chamber) typically ranges from about 5 µL to about 100 µL, more typically from about 5 µL to about 60 µL. The typical range of prostaglandin in the formulation ranges from 0.1% to 5% (w/w). Thus, the practitioner can select a formulation based on concentration of drug in the formulation, the size of the unit dosage, or both, to deliver prostaglandin for a desired length of time. This also allows a dosing regimen in which the re-administration of the formulation can be determined by considering the patient's needs, the sustained release profile of the formulation, and the therapeutic effect observed by the physician. For example, a patient can receive an injection about every 60 days (two months), 90 days (three months), 120 days (four months), or as the physician directs. Typically, intraocular injections (into the anterior chamber or vitreous) of the prostaglandin/benzyl benzoate formulations described herein are administered no more frequently than once every two months, once every three months, once every four months, etc., to once every twelve months. An example treatment schedule for a human patient comprises of one intravitreal injection of about 25 µL of a formulation consisting solely of 0.1% to 1% (w/w) latanoprost in benzyl benzoate, which may be repeated no more frequently than once every two months. Additionally, the pharmacological effect may last beyond the disappearance of the dosage form.

When administered into the eye via intravitreal injection, the substantially clear, liquid formulation maintains a monolithic form (e.g., a droplet or roughly spherical shape) that remains in the bottom of the eye, effectively out of the patient's vision. The same is true when the formulation is injected into the anterior chamber of the eye. After injection into either site, the formulation steadily releases prostaglandin to the aqueous humour in the anterior chamber of the eye, where it acts to relieve intraocular pressure. Because the dose is constant and delivered accurately, formulations containing relatively low amounts of drug can be used, even delivering picograms of prostaglandin to the anterior chamber. The practitioner can observe the dosage form within the patient's eye, and prostaglandin is released as long as the formulation is present. This allows for ease in monitoring the medicine in relation to the intraocular pressure, and allows for accurate dosing information. This also assists the physician in scheduling re-administration in a dosage regimen. Moreover, prostaglandin levels can be adjusted by adjusting the size of the unit dose or the concentration of the prostaglandin in the dose. A specific embodiment consisting of latanoprost in benzyl benzoate is an injectable liquid formulation.

In a particular embodiment, the present invention provides for a medicament for the treatment of elevated intraocular pressure or glaucoma, the medicament consisting of 0.1% to 5% (w/w %), inclusive, of a prostaglandin in benzyl benzoate, for intravitreal injection in a dosing regimen that consists of injecting into the vitreous of the eye a dosage volume of the medicament ranging from 5 µL to 60 µL, inclusive, no more frequently than once every two months.

DETAILED DESCRIPTION

Figure 1:
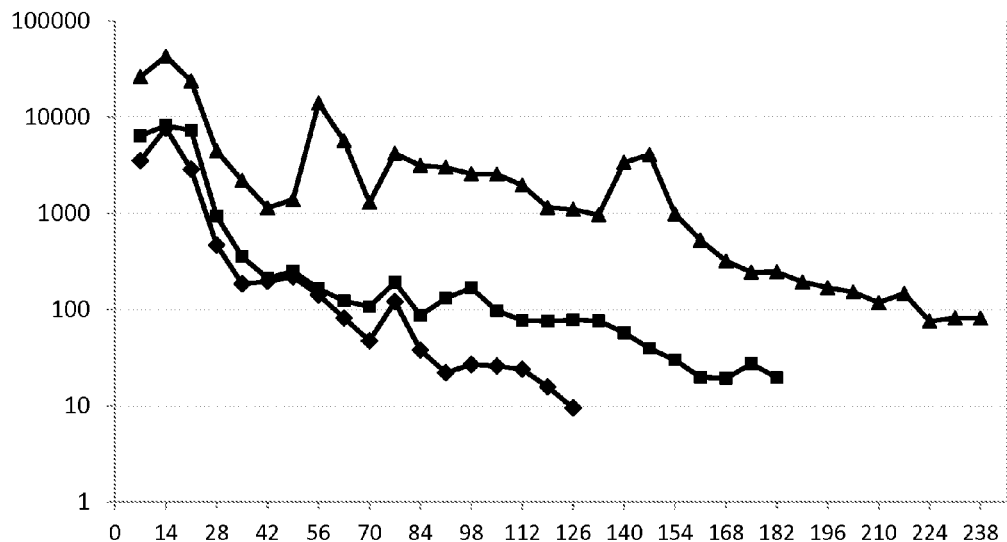
FIG. 1 shows the in vivo release profiles of latanoprost (pg/mL) from three formulations of latanoprost in benzyl benzoate (Lat/BB) administered as a single, 50 µL injection. y-axis: concentration of latanoprost acid in the aqueous humour (pg/mL); x-axis: days; ♦1% (w/w %) Lat/BB; ■2% Lat/BB; ▲4% Lat/BB.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

The major risk factor for most glaucomas, and focus of treatment, is increased intraocular pressure, i.e., ocular hypertension. Intraocular pressure is a function of production of liquid aqueous humour by the ciliary processes of the eye, and its drainage through the trabecular meshwork. Aqueous humour flows from the ciliary processes into the posterior chamber, bounded posteriorly by the lens and the zonules of Zinn, and anteriorly by the iris. It then flows through the pupil of the iris into the anterior chamber, bounded posteriorly by the iris and anteriorly by the cornea. From there, the trabecular meshwork drains aqueous humour via Schlemm's canal into scleral plexuses and general blood circulation.

Eye pressure is measured in millimeters of mercury (mm Hg). Normal eye pressure ranges from 12-22 mm Hg, and eye pressure of greater than 22 mm Hg is considered higher than normal.

In open/wide-angle glaucoma, flow is reduced through the trabecular meshwork, due to the degeneration and obstruction of the trabecular meshwork, whose original function is to absorb the aqueous humour. Loss of aqueous humour absorption leads to increased resistance and thus a chronic, painless buildup of pressure in the eye. In close/narrow-angle glaucoma, the iridocorneal angle is completely closed because of forward displacement of the final roll and root of the iris against the cornea, resulting in the inability of the aqueous fluid to flow from the posterior to the anterior chamber and then out of the trabecular network. This accumulation of aqueous humour causes an acute increase of pressure and pain.

As noted above, the trabecular meshwork is a tiny spongy tissue that allows fluid to leave the eye via the anterior chamber. The trabecular meshwork is assisted to a small degree in the drainage of aqueous humour by a second outflow pathway, the uveoscleral pathway (5-10% of outflow occurs this way). The uveoscleral pathway is increased (i.e., opened) with the use of glaucoma drugs such as prostaglandin agonists. Such prostaglandins are used routinely in lowing intraocular pressure in open-angle glaucoma, but these medications are also indicated in angle-closure glaucoma if a safe intraocular pressure level can not be reached after angle-opening procedures. Prostaglandins work by affecting the aqueous drainage system within the eye to increase aqueous outflow which, in turn, lowers intraocular pressure (IOP). Currently, when delivered to the eye as an eye drop, the drug goes into the anterior chamber where it is active.

Selective prostaglandin analogs became generally available as eye drops for the treatment of glaucoma in 1996. These include latanoprost (marketed as Xalatan® by Pfizer), bimatoprost (prostamide analog, marketed as Lumigan® by Allergan), travoprost (fluprostenol isopropyl ester, available from Cayman Chemical, Ann Arbor, Mich.; marketed as Travatan Z® by Alcon), unoprostone (marketed as Rescula® by Sucampo Pharma Americas, Inc.), tafluprost (marketed as Zioptan™ by Merck), prostaglandin $E_1$ (alprostadil), and prostaglandin $E_2$ (dinoprostone). Other prostaglandin analogs for medicinal use include cloprostenol. See also WO/2011/046569, Process for the preparation of F-series prostaglandins.

Thus, as used herein, the term "prostaglandin" includes FP-receptor agonists, prostamide receptor agonists, prostaglandins, prostaglandin analogs, prostamides, prostamide analogs, and prodrugs and active metabolites of these. In specific embodiments, the prostaglandin is latanoprost. Because the prostaglandins are similar in chemical structure, it is expected that one skilled in the art can formulate these drugs in benzyl benzoate (and benzyl benzoate equivalents) as described herein without undue experimentation.

Latanoprost and travoprost are actually prostaglandin prodrugs (i.e., 1-isopropyl esters of a prostaglandin) but they are referred to as prostaglandins because they act on the prostaglandin FP-receptor after being hydrolyzed to the 1-carboxylic acid. Latanoprost is currently available in a generic form. In the eye, latanoprost is rapidly hydrolyzed to the active form, latanoprost acid, by endogenous esterase enzymes. Its chemical name is isopropyl-(Z)7[(1R,2R,3R,5S) 3,5-dihydroxy-2-

[(3R)-3-hydroxy-5-phenylpentyl]cyclopentyl]-5-heptenoate. Its molecular formula is $C_{26}H_{40}O_5$, molecular weight 432.58, and its chemical structure is:

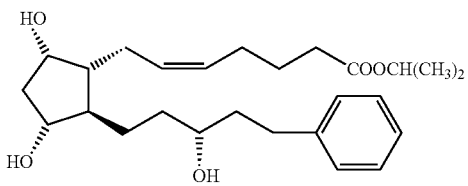

Latanoprost is a colorless to slightly yellow oil that is very soluble in acetonitrile and freely soluble in acetone, ethanol, ethyl acetate, isopropanol, methanol, and octanol. It is practically insoluble in water. Latanoprost and other prostaglandin analogs are available commercially, for example, from Cayman Chemical (Ann Arbor, Mich.).

Particular formulations embodied herein provide for liquid latanoprost in the liquid excipient benzyl benzoate. Benzyl benzoate is a biocompatible, biodegradable, bioerodible, low solubility excipient that provides for a conveniently injectable sustained release formulation for many active agents. Other benzoates that are envisioned for use in place of or with benzyl benzoate include ethyl benzoate, n-propyl benzoate, isopropyl benzoate, n-butyl benzoate and isobutyl benzoate. See U.S. Pat. No. 7,906,136; U.S. Patent Publication No. 2008/0038316. Use of this single, liquid excipient is advantageous over complex polymers used currently in other sustained release devices and formulations. The present formulations are configured to release the latanoprost for extended periods of time at relatively steady rates compared to commercially available eye drop formulations. In some embodiments, the latanoprost is released at a substantially linear rate (e.g., a single rate) over many weeks or months (i.e., until the monolithic dosage form degrades).

When the prostaglandin/benzyl benzoate liquid formulation is injected slowly into the vitreous or anterior chamber of the eye, monolithic integrity is maintained and a uniform liquid reservoir is formed. This liquid reservoir maintains its integrity and in vivo "breakage" has not been observed ophthalmoscopically. In other words, the formulation does not break up as a multitude of smaller droplets or particles that migrate away from the intended point of placement or by virtue of a resultant increase in surface area greatly alter the intended release rate of the drug content. The dosage form is placed in the eye where it does not obscure patient vision. The dosage form can be observed in the eye by the physician, however, and as long as the formulation is visible in the eye the prostaglandin is being released. None of the composition remains at the end of therapy, which facilitate the administration of additional doses, as most major ophthalmic diseases are chronic in nature.

In particular embodiments, the liquid formulations are, for example, 0.1% 0.25%, 0.5%, 1%, 2%, 3%, 4%, or 5% (w/w %) equivalent latanoprost, inclusive, in benzyl benzoate. In other words, example weight ratios of latanoprost:benzyl benzoate of the formulations described herein can be, for example, 0.1:99.9, 0.25:99.75, 0.5:99.5, 1:99, 2:98, 3:97, 4:96, or 5:95, or ranges in between, such as 2.5:97.5 latanoprost:benzyl benzoate (w:w).

Unit dose sizes for injection into the vitreous or anterior chamber are generally in the range of 50 µL to 60 µL, inclusive; and typically in the range of 20 µL to 40 µL, inclusive. Volumes equal to or larger than 100 µL are typically not injected into the eye, but in some instances volumes in excess of 100 µL may be warranted. Thus, for example, unit dosage volumes in some embodiments can be about 5 µL, 10 µL, 20 µL, 25 µL 30 µL, 40 µL, 50 µL, 60 µL, 70 µL, 80 µL, 90 µL, or 100 µL, or a volume included within this range. A particular dosage form or unit consists of about 20 µL to 25 µL, of a concentration selected from 0.1% to 1.0% latanoprost (w/w), inclusive, in benzyl benzoate, such as a dosage form consisting of about 25 µL, of 0.5% latanoprost in benzyl benzoate.

Additionally, the w/w % may be adjusted according to the nature of the latanoprost source and reflect volume, percentage and weight of a formulation. For example, a unit dosage may be expressed as 20 µL of 1% latanoprost intravitreal injection, 224 µg equivalent latanoprost dose; 50 µL of 1% latanoprost intravitreal injection, 559 µg equivalent latanoprost dose; 20 µL of 2% latanoprost intravitreal injection, 447 µg equivalent latanoprost dose; 50 µL of 2% latanoprost intravitreal injection, 1118 µg equivalent latanoprost dose; 20 µL of 4% latanoprost intravitreal injection, 894 µg equivalent latanoprost dose; or 50 µL of 4% latanoprost intravitreal injection, 2236 µg equivalent latanoprost dose; or the like.

A syringe apparatus including an appropriately sized needle, for example, a 22 gauge needle, a 27 gauge needle, or a 30 gauge needle, can be effectively used to inject the formulation into the vitreous or anterior chamber of the eye. Frequent repeat injections are often not necessary due to the sustained release of the latanoprost from the formulation. The injection process is standard and relatively fast, and does not require additional surgical procedures. The accuracy in delivery of small volumes to the eye may be aided by use of a dose guide for an injection syringe, for example, as taught in publication WO 2012/149040.

Specific example unit dose formulations of latanoprost (w/w %) in benzyl benzoate include 5 µL 1% latanoprost; 20 µL to 25 µL 0.1% latanoprost; 20 µL to 25 µL 0.25% latanoprost; 20 µL to 25 µL 0.5% latanoprost; 20 µL to 25 µL 1% latanoprost; 30 µL 0.5% latanoprost; 30 µL 1% latanoprost; 30 µL 2% latanoprost; 30 µL 4% latanoprost; 50 µL 0.5% latanoprost, 50 µL 1% latanoprost (558 µg/50 µL); 50 µL 2% latanoprost (1118 µg/50 µl); and 50 µL 4% latanoprost (2236 µg/50 µl). One skilled in the art appreciates that there may be some minor variations in the unit dose volume without deviating from the embodiments of the invention, and that the sustained release of the latanoprost is achieved.

The formulations of the present invention can be easily injected into the anterior chamber, posterior segment, vitreous, or vitreous chamber of the eye. By injecting the prostaglandin-containing formulation into the posterior segment of an eye, it is believed that the prostaglandin (e.g., latanoprost) is effective to enhance aqueous humour flow thereby reducing intraocular pressure. Without being bound by theory, intravitreal administration may be particularly advantageous in treating glaucoma because it takes advantage of the eye's natural fluid flow: the vitreous humour delivers the prostaglandin to the trabecular meshwork and uveoscleral pathway as it flows to the anterior chamber. This provides for delivery of the active agent to the site of action within the eye. By contrast, in subconjunctival administration such as implantation or injection within the anterior sub-tenon space of the eye, the active agent must pass through the sclera of the eye. Similarly, eye drops are notoriously inefficient at delivering agent to the anterior chamber: in current commercial glaucoma eye drops, only 1% of the active agent penetrates the tissues against the outward flow and pressure of the anterior chamber.

Dosing regimens include one injection of a prostaglandin (such as latanoprost) in benzyl benzoate once every two months (about every 60 days or 8 weeks), once every three months (about every 90 days or 12 weeks), once every four months (about every 120 days or 16 weeks), once every five months (about every 150 days), once every six months (about every 180 days), once every seven months (about every 210 days), once every eight months (about every 240 days), once every nine months (about every 270 days), once every ten months (about every 300 days), once every eleven months (about every 330 days), or once every twelve months (about every 360 or 365 days, or every 52 weeks), or at periods within these months, weeks, or days as determined by the prescribing physician in monitoring intraocular pressure and disease state. In commercial practice, treatment regimens may likely be adjusted by dose volume size or time between injections, rather than prostaglandin concentration, but in any event will not require intravitreal injection more frequently than once every two months.

The formulations presented herein can also be administered with other therapy approaches to treating an ocular condition, for example, administering additional therapeutic agents to the eye, such as by topically administering compositions containing a carbonic anhydrase inhibitor (e.g., brinzolamide or dorzolamide) or a beta-adrenergic receptor antagonist (e.g., timolol). These additional therapies may be administered as eye drops, sustained release eye drops (see, e.g., U.S. Pat. No. 8,541,413), implants or ocular injections into, for example, the subconjunctiva, periocular space, retrobulbar in the orbit, episclera, intracomea, intrasclera, anterior chamber, anterior segment, posterior chamber, posterior segment, vitreous cavity, subretinal space, suprachorodial segment or intraretinal area of the eye (see, e.g., U.S. Pat. No. 7,906,136) as are known in the art.

EXAMPLES

Example 1

In Vivo Release of Latanoprost from Benzyl Benzoate

Liquid formulations of latanoprost and benzyl benzoate were made by weighing each component and mixing them together. Latanoprost is soluble in benzyl benzoate, yielding a clear solution. The formulations were either 1%, 2%, or 4% (w/w %) latanoprost.

Figure 2:
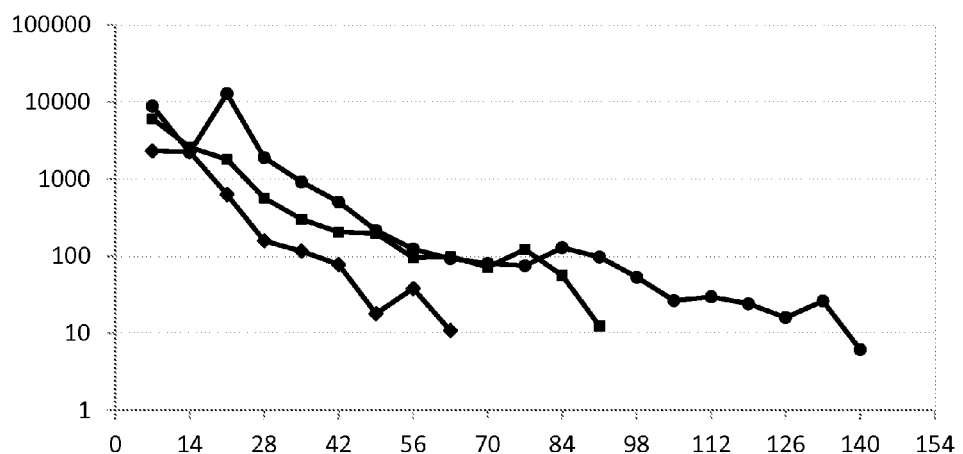
FIG. 2 shows the in vivo release profiles of latanoprost (pg/mL) from three formulations of latanaprost in benzyl benzoate administered as a single, 30 µL injection. y-axis: concentration of latanoprost acid in the aqueous humour (pg/mL); x-axis: days; ♦1% Lat/BB (w/w %); ■2% Lat/BB; ●4% Lat/BB.

Either 30 µL or 50 µL of each formulation was injected only once into the posterior segment of the eyes of rabbits (five rabbits per formulation per dosage size; thirty rabbits). Weekly, the aqueous humour of treated eyes was collected, generally about 100 µL to 150 µL in volume, pooled, concentrated 10-fold, and analyzed by liquid chromatography-mass spectrometry (LCMS) to afford the level of latanoprost acid (the active form of the drug) released into the aqueous humour. The concentration of the latanoprost (pg/mL) in the samples of aqueous humour from the single, 50 µL intravitreal injection are shown in FIG. 1. The concentration of the latanoprost (pg/mL) in the samples of aqueous humour from the single, 30 µL intravitreal injection are shown in FIG. 2. In each test, including the single injection of 30 µL 1% latanoprost, latanoprost was detected in the aqueous humour in a concentration of at least 10 pg/mL for at least 60 days.

Figure 3:
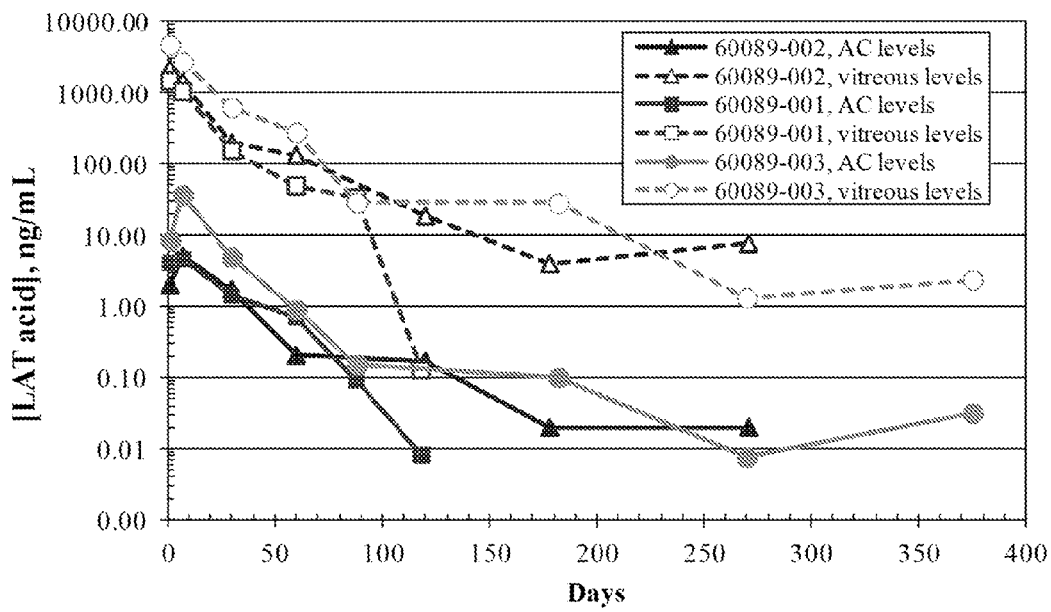
FIG. 3 compares in vivo release profiles of latanoprost (ng/mL) from three formulations of 1%, 2% or 4% latanoprost (% Lat w/w) in benzyl benzoate; administered as a single, 50 µL intravitreal injection into rabbit eyes. Samples of the humour of the anterior chamber (AC) and vitreous humour were collected on the days indicated. y-axis: concentration of latanoprost acid in the sample; x-axis: days; ■1% Lat AC levels; □1% Lat vitreous levels; ▲2% Lat AC levels; Δ2% Lat vitreous levels; ●4% Lat AC levels; ○4% Lat vitreous levels.

In another in vivo experiment, formulations of either 1%, 2%, or 4% (w/w %) latanoprost in benzyl benzoate were prepared. A dose of 50 µL of each formulation was injected only once into the posterior segment/vitreous (i.e., intravitreal injection) of the eyes of test rabbits. Thereafter, samples were collected from the aqueous humour from the anterior chamber and from the vitreous humour, and were analyzed for latanoprost acid as described above. As shown in FIG. 3, even the lowest concentration of latanoprost (1% w/w %) exhibited sustained release into the anterior chamber of the eye for at least sixty days (two months). One skilled in the art can readily extrapolate a sustained release profile from these Figures.

Example 2

Intraocular Pressure Reduction

Figure 4:
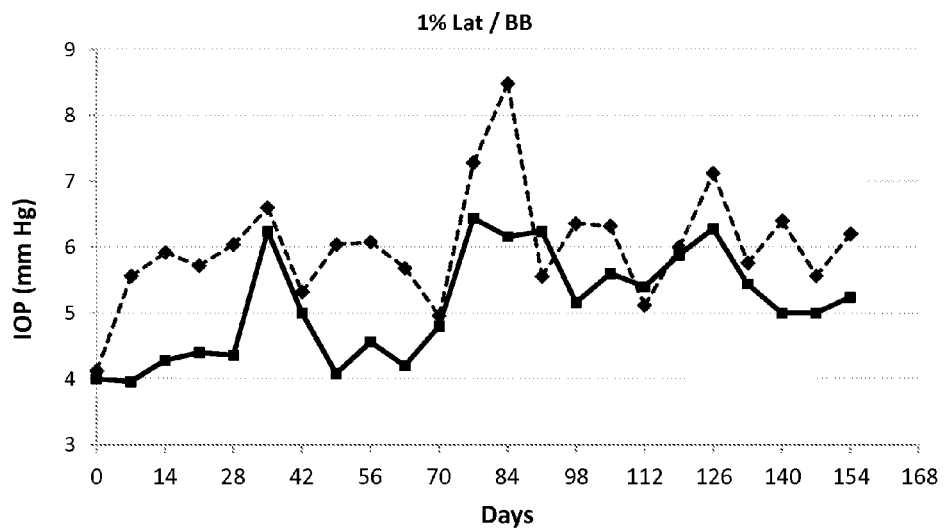
FIG. 4 compares the weekly intraocular pressure (IOP [mm hg]) of rabbits' untreated eyes (♦) with eyes injected with 50 µL, of 1% (w/w %) latanoprost in benzyl benzoate (■) over the course of 22 weeks.
Figure 5:
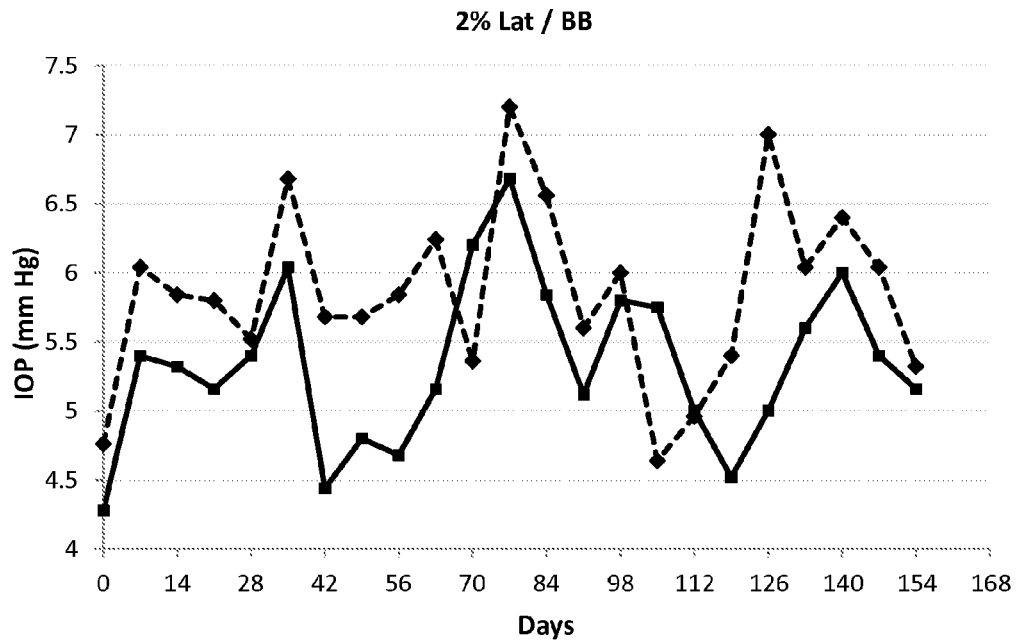
FIG. 5 compares the weekly intraocular pressure (IOP [mm hg]) of untreated eyes (♦) with eyes injected with 50 µL, of 2% (w/w %) latanoprost in benzyl benzoate (■) over the course of 22 weeks.
Figure 6:
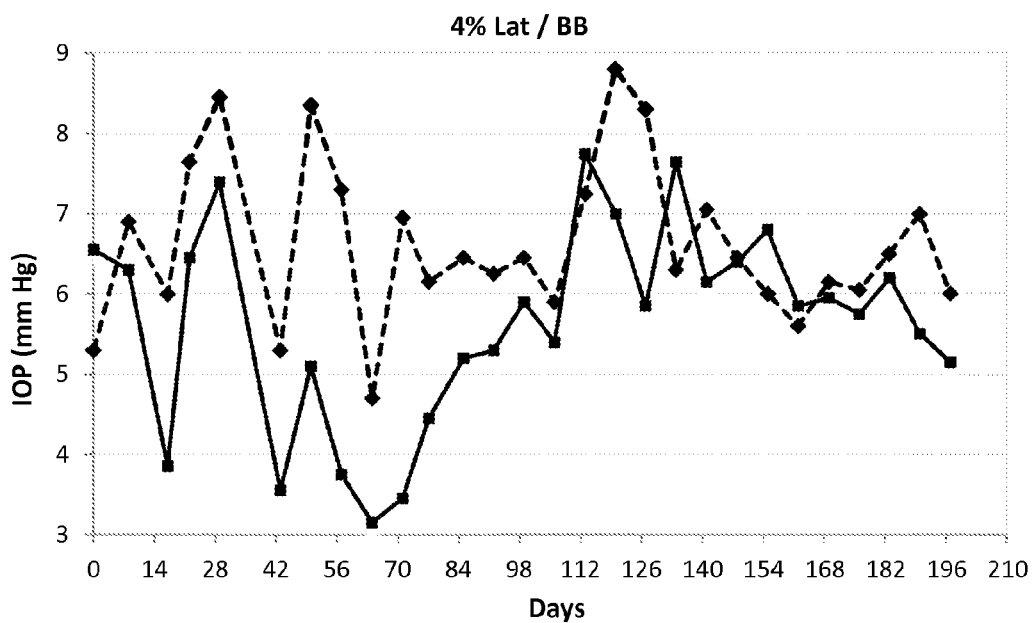
FIG. 6 compares the weekly intraocular pressure (IOP [mm hg]) of untreated eyes (♦) with eyes injected with 50 µL, of 4% (w/w %) latanoprost in benzyl benzoate (■) over the course of 28 weeks.

To assess the effect on intraocular pressure, five rabbits were used per 1%, 2% or 4% latanoprost/benzyl benzoate formulation, and 50 µL aliquots were injected into the posterior segment of only the left eye of each animal. The right eyes were not treated, and served as control. Each week, each eye's intraocular pressure was measured using an iCare Tonometer 5×. Measurements were averaged for each time point. As shown in FIGS. 4-6, at almost all time points the intraocular pressure in the treated eyes was lower than the pressure in the untreated eyes, even 154 days after the single injection. Overall, intraocular pressure remained lower in the treated eye compared with the untreated eyes for 196 days in the rabbits treated with 50 µL 4% latanoprost.

Additionally, three-month toxicology reports indicated that none of the latanoprost/benzyl benzoate formulations had any toxic effect in the eyes or bodies of the rabbits.

Example 3

Sustained Release Prostaglandin Formulations

The present prostaglandin benzyl benzoate formulations for intravitreal injection are used in the treatment patients with open-angle glaucoma, pseudoexfoliative glaucoma, pigmentary glaucoma, or ocular hypertension. Dose escalation in a clinical trial setting is used to determine the optimal concentration for commercial production. For example, 5 µL of a 1% latanoprost represents a starting dose; and the concentration or volume or both are stepped-up as required to determine the optimal concentration of latanoprost that achieves the desired clinical outcome (e.g., safety, pharmacokinetic, and pharmacodynamic parameters) over a study population, as confirmed in a randomized clinical study. The maximum concentration envisioned herein is about 5% latanoprost (w/w %) and the maximum dose volume is about 100 µL. For example, an effective dose for intravitreal injection no more frequently than once every two months may be between 20 µL to 60 µL of latanoprost in a concentration range between 0.1% and 4% (w/w %), inclusive, such as about 25 µL of 0.50% latanoprost. It is likely that a commercially relevant concentration is determined, and thereafter a dosing regimen is recommended based on adjusting dose volume and frequency of injections. For example, the formulation as initially administered may be re-administered once the preceding dose is no longer visible by physician, depending on therapeutic outcome. Moreover, one skilled in the art is aware that the pharmacological effect of the treatment may last beyond the time at which the sustained release formulation has fully bioeroded.

Further regarding dose and administration, the intravitreal injection of sustained release prostaglandin is carried out under aseptic conditions, using sterile drape, sterile gloves, and sterile eyelid speculum. Under current best practices, proper anesthesia and povidone-iodine are administered before the injection. During the injection, the physician wears a surgical mask. After injection, the patient is monitored for intraocular pressure. Ocular examination by indirect ophthalmoscopic examination is performed following the injection of drug. The patient is instructed to report any symptoms of pain or redness suggestive of an infection (endophthalmitis) immediately to their ophthalmologist.

Efficacy outcome measure include intraocular pressure (IOP) is currently the accepted standard for establishing the efficacy of ocular hypotensive medications. IOP is a surrogate end point for potential visual function loss. For equivalence trials efficacy is attained if the difference in mean IOP between treatment groups is within ±1.50 mm Hg at all post-baseline time points; and within ±1.00 mm Hg at the majority of post-baseline time points. This regulatory requirement for equivalence has been consistently used for the approval of several IOP lowering products over many years.

We claim:

1. A method of treating elevated intraocular pressure or glaucoma in a subject in need of such treatment comprising administering by intraocular injection into the vitreous or anterior chamber a unit dose of 5 µL to 60 µL, inclusive, of a liquid formulation consisting of about 0.1% to 5% prostaglandin in benzyl benzoate (w/w), inclusive, no more frequently than once every two months.

2. The method of claim 1, wherein the prostaglandin in said liquid formulation is latanoprost, wherein a unit dosage of latanoprost is expressed as 224 µg, 447 µg, 559 µg, 894 µg, 1118 µg or 2236 µg equivalent latanoprost dose.

3. The method of claim 2, wherein the unit dose is about 20 µL to 25 µL and the formulation contains a concentration of latanoprost selected from a range of about 0.1% to 1% latanoprost (w/w), inclusive.

4. The method of claim 3, wherein the unit dose is administered no more frequently than once every three months.

5. The method of claim 1, wherein the unit dose is administered no more frequently than once every six months.

6. The method of claim 2, wherein a unit dose of 5 µL to 60 µL of said liquid formulation of latanoprost is equivalent to about 0.1%, 0.25%, 0.5%, 1%, 2%, 3% 4% or 5% (w/w %) of latanoprost, inclusive in benzyl benzoate (w/w).

7. The method of claim 6, wherein a unit dose of 20 µL of 1% latanoprost (w/w), inclusive is equivalent to about 224 µg of latanoprost dose.

8. The method of claim 6, wherein a unit dose of 50 µL of 1% latanoprost (w/w), inclusive is equivalent to about 559 µg of latanoprost dose.

9. The method of claim 6, wherein a unit dose of 20 µL of 2% latanoprost (w/w), inclusive is equivalent to about 447 µg of latanoprost dose.

10. The method of claim 6, wherein a unit dose of 50 µL of 2% latanoprost (w/w), inclusive equivalent to about 1118 µg of latanoprost dose.

11. The method of claim 6, wherein a unit dose of 20 µL of 4% latanoprost (w/w), inclusive is equivalent to about 894 µg of latanoprost dose.

12. The method of claim 6, wherein a unit dose of 50 µL of 4% latanoprost (w/w), inclusive is equivalent to about 2236 µg of latanoprost dose.

* * * * *